(12) United States Patent
Gregoriadis et al.

(10) Patent No.: US 7,008,791 B1
(45) Date of Patent: Mar. 7, 2006

(54) LIPOSOME-ENTRAPPED DNA ORAL VACCINES

(75) Inventors: Gregory Gregoriadis, London (GB); Yvonne Perrie, Birmingham (GB)

(73) Assignee: Lipoxen Technologies Limited, (GB)

( * ) Notice: Subject to any disclaimer, the term of this patent is extended or adjusted under 35 U.S.C. 154(b) by 127 days.

(21) Appl. No.: 10/089,312

(22) PCT Filed: Oct. 2, 2000

(86) PCT No.: PCT/GB00/03773

§ 371 (c)(1),
(2), (4) Date: Mar. 29, 2002

(87) PCT Pub. No.: WO01/24773

PCT Pub. Date: Apr. 12, 2001

(30) Foreign Application Priority Data

Oct. 1, 1999 (EP) .................................. 99307786

(51) Int. Cl.
*C12N 15/88* (2006.01)
*A61K 9/127* (2006.01)

(52) U.S. Cl. ...................... 435/458; 424/450; 435/455; 514/44

(58) Field of Classification Search ................ 424/450; 514/44; 435/320.1, 455, 458
See application file for complete search history.

(56) References Cited

U.S. PATENT DOCUMENTS

2002/0151070 A1 * 10/2002 Bischoff et al. ............ 435/458

FOREIGN PATENT DOCUMENTS

WO    WO 98/10748    3/1998

OTHER PUBLICATIONS

Reyes-Sandoval, Current Molecular Medicine, vol. 1, pp. 217-243, 2001.*
Pachuk, Current Opinion in Molecular Therapeutics, 2, 2, 188-198, 2000.*
McCluskie et al. (Molecular Medicine, 5, pp. 287-300, 1999).*
Gregoriadis et al., "Vaccine Entrapment in Liposomes", Methods 19 pp. 156-162 (1999).
Perrie et al., "Genetic Immunization Using Liposome-Incorporated DNA", J. Pharm. Pharmacol. 50 (Supplement) 103 (1998).
Gregoriadis et al., "Liposome-Mediated DNA Vaccination", FEBS Letters 402, pp. 107-110 (1997).
Han et al., "Application of Liposomes for Development of Oral Vaccines: Study of In Vitro Stability of Liposomes and Antibody Response to Antigen Associated with Liposomes After Oral Immunization" Journal of Veterinary Medical Science vol. 50 No. 12 (Dec. 1997).

* cited by examiner

Primary Examiner—Janet L. Epps-Ford
Assistant Examiner—D Jacobs
(74) Attorney, Agent, or Firm—Dickstein, Shapiro, Morin & Oshinsky, LLP.

(57) ABSTRACT

An oral vaccine contain liposomes and complexed or, preferably entrapped, DNA operatively encoding an antigen in which the liposomes are formed from components including cationic compounds and zwitterionic phospholipids. The hydrophobic groups within the liposome forming components must include at least one group which is saturated. This is believed to raise the transition temperature, rendering the liposomes more stable when delivered orally. The compositions have been found to give detectable increased in IgA levels, secreted immunoglobulins of importance in efficacious oral vaccine delivery.

20 Claims, 5 Drawing Sheets

Fig 2d 60 days
Fig. 3a 70 days
Fig. 3b

LIPOSOME-ENTRAPPED DNA ORAL VACCINES

BACKGROUND OF THE INVENTION

The present invention relates to oral vaccines comprising cationic liposomes and, complexed or entrapped within the liposomes, a gene vaccine, that is a nucleic acid coding for an antigen against which vaccination is desired.

In WO-A-9810748 gene vaccines are described comprising nucleic acid encoding antigen against which vaccination is required, in which the nucleic acid is entrapped within the liposomes. The liposomes are formed from liposome forming components including cationic lipid. The compositions are said to be suitable for administration by, inter alia, oral routes but in the examples, the compositions are administered intramuscularly, subcutaneously, intravenously or intraperitoneally.

For a vaccine to generate an immune response following oral administration, the composition must interact with the lymphoid system in the gut. The vaccine must consequently be stable in the GI tract, and must be stable enough to interact with the relevant cells of the system before being destroyed by bile salts. Clearly it is desirable for vaccines to be administratable orally rather than having to be injected. The present invention relates to compositions which are suitable for oral administration and to oral vaccines and methods for vaccinating human or non human animals by oral administration of the vaccines.

DESCRIPTION OF THE INVENTION

According to a first aspect of the invention there is provided a novel vaccine comprising a nucleic acid operatively encoding an antigen complexed with and/or entrapped within liposomes formed from liposome forming components including a) at least one cationic compound having the general formula I,

I in which $R^1$ and $R^2$ are the same or different and are selected from groups of the formula $CH_3(CH_2)_a(CH=CH-CH_2)_b(CH_2)_c(CO)_d-$
in which b is 0 to 6, a and c are each selected from 0–23 and (a+c+3b) is in the range 12–23 and d is 0 or 1;
$R^5$ is a bond or a $C_{1-8}$ alkanediyl group a $C_{1-4}$ alkoxy-$C_{1-4}$ alkyl group, or a $C_{1-8}$ oxy-alkylene group;
$X^1$ is N, P or S;
n is 3 where $X^1$ is N or P and is 2 where $X^1$ is S; and
the groups $R^6$ are the same or different and are selected from hydrogen, $C_{1-8}$ alkyl, $C_{6-12}$ aryl or aralkyl, or two or three of the groups $R^6$ together with $X^1$ may form a saturated or unsaturated heterocyclic group having 5 to 7 ring atoms;

b) at least one zwitterionic phospholipid having the general formula II

II in which $R^3$ and $R^4$ are the same or different and are selected from groups of the formula $CH_3(CH_2)_e(CH=CH-CH_2)_f(CH_2)_g-$
in which f is 0 to 6, each of e and g are 0 to 23 and (e+g+3f) is in the range 12 to 23;
$R^7$ is a $C_{1-8}$ alkanediyl group;
Y is —O— or a bond;
$X^2$ is N, P or S;
m is 3 when $X^2$ is N or P and is 2 when $X^2$ is S; and
the groups $R^8$ are the same or different and are selected from the group consisting of hydrogen, $C_{1-8}$ alkyl, $C_{6-11}$ aryl or aralkyl, or two or three of the groups $R^8$ together with $X^2$ may form a saturated or unsaturated heterocyclic group having 5 to 7 ring atoms;
provided that in at least one of the groups $R^1$, $R^2$, $R^3$ and $R^4$, b or f, as the case may be, is 0.

The composition is preferably an oral vaccine and the invention also covers methods of administering the vaccine by oral routes. The composition may comprise pharmaceutically acceptable diluents, and may include components to enhance the immunogenic properties of the vaccine, such as conventional adjuvants.

In the invention the proviso that at least one of the groups $R^1$, $R^2$, $R^3$ and $R^4$ should have an saturated long chain alkyl group tends to provide a composition which has a relatively high transition temperature. Thus the liposome forming components, in admixture, should have a transition temperature of at least 37° C., preferably in the range 38 to 50° C.

It is preferred that the groups $R^1$ and $R^2$ are the same as one another and that the groups $R^3$ and $R^4$ are the same as one another. In general the present inventors have found that it is desirable that either $R^1$ and $R^2$ are unsaturated and $R^3$ and $R^4$ are saturated, or vice versa. Preferably the cationic compound comprises a single compound of the formula I.

In a particular embodiment of the invention two zwitterionic phospholipids having a different formula, each within formula II, are used in the liposome forming components.

In one embodiment wherein such a mixture is used, in a first zwitterionic phospholipid, the groups $R^3$ and $R^4$ are the same and each represent a group, which f is 1, and in which e+g is in the range 14 to 20, preferably in the range 14 to 18. Preferably the unsaturated group is midway along $R^3$ or $R^4$ that is e≈g, preferably e=g=7. Usually the ethylenic bond is cis.

In a second embodiment wherein a mixture of phospholipids is used in the first phospholipid of a mixture, the groups $R^8$ are preferably all the same and are preferably hydrogen. In the second phospholipid of the formula II, the groups $R^8$ are all the same and are $C_{1-4}$-alkyl. Often in this embodiment, for both phospholipids, f is 0.

Generally, in both embodiments using mixtures of phospholipids in both first and second phospholipids, Y is O and $X^2$ is N. Furthermore $R^7$ is preferably $C_{2-3}$-alkanediyl.

In the cationic compound of the formula I, the hydrophobic groups $R^1$ and $R^2$ may be joined to the rest of the molecule through ether linkages (that is d is 0) or ester linkages (in which d is 1). Preferably in compounds of the formula I, $R^5$ is $C_{1-4}$-alkanediyl. Preferably the cationic compound is permanently cationic, that is substantially fully ionised at all pH's likely to be encountered in vivo, in the range 5 to 9. Preferably each of the group $R^6$ is other than hydrogen, therefore, especially $C_{1-4}$-alkyl, most preferably each group $R^6$ being methyl.

$R^5$ is preferably a bond or a methylene group.

A particularly preferred embodiment of the composition of the invention utilises a cationic compound of the general formula I in which each of the groups $R^1$ and $R^2$ is an oleoyl group, and in which the group $R^5$ is a bond, $X^1$ is N and each of the groups $R^6$ is methyl (1,2-bis(oleoyloxy)-3-(trimethylammonio)propane(DOTAP)). An alternative cationic compound is the analogous compound in the which the hydrophobic oleoyl groups are replaced by oleyl groups i.e. joined through ether linkages rather than ester linkages. A suitable cationic compound in which the hydrophobic groups are saturated is 1,2-bis(hexadecyloxy)-3-trimethylammino propane(Bis HOP).

Suitable zwitterionic phospholipids include dioleoyloxy phosphatidyl ethanolamine (DOPE), dioleoyloxy phosphatidylcholine (DOPC), distearoyl phosphatidyl ethanolamine (DSPE), distearoyloxy phosphatidylcholine (DSPC), dipalmitoyl phosphatidyl ethanolamine (DPPE), dipalmitoyl phosphatidylcholine (DPPC), and admixtures. A particularly preferred zwitterionic phospholipid mixture comprises distearoyl phosphatidylcholine and dioleoyl phosphatidyl ethanolamine.

A mixture of two zwitterionic phospholipids generally comprises the two compounds in weight ratios in the range 10:1 to 1:10, most preferably in the range 5:1 to 1:5, more preferably 2:1 to 1:2. Preferably the proportion of groups $R^3$ and $R^4$ which are saturated in a mixture is at least 50%.

Generally the ratio of cationic compound to zwitterionic phospholipid (total) is in the range 10:1 to 1:20, more preferably in the range 5:1 to 1:10, more preferably in the range 1:1 to 1:5.

According to a further aspect of the invention there is provided an oral vaccine comprising a nucleic acid encoding an antigen complexed to and/or entrapped within liposomes formed from liposome forming components including at least one glycerolipid, at least one cationic compound and at least one zwitterionic phospholipid characterised in that the glycerolipid is an O,O'-dialkanoyl or O,O'-dialkyl phospholipid. Preferably the glycerolipid is a compound of the general formula II above in which, in both $R^3$ and $R^4$ f is 0.

In all aspects of the invention it is preferred that the liposome forming components in combination have a transition temperature of at least 37° C. Transition temperatures are determined by differential scanning calorimetry.

In this aspect of the invention the zwitterionic phospholipids preferably comprise a mixture of lipids, for instance a mixture of saturated and unsaturated lipids, and/or a mixture of phosphatidylcholines and phosphatidylethanolamines.

The cationic compound is preferably a 2,3-di(acyloxy or alkoxy) substituted propylamine derivative, for instance having the general formula I above. Alternatively the compound may be formed of simple cationic amphiphilic compounds such as mono- or di-stearylamine or other long chain alkyl amine, or the secondary, tertiary or quaternary derivatives thereof having, respectively, one, two or three N-lower alkyl ($C_{1-4}$ alkyl) substituents, such as dimethyldioctadecyl ammonium halides. Another category of amphiphilic cationic compounds which are suitable for incorporating into liposomes, is spermine conjugates with di(fatty acyl) glycerides or N,N-di($C_{12-24}$) alkyl acyl amide compounds or 3β-[N-(N',N'-dimethylaminoethane)-carbamyl]cholesterol (DC chol). A range of suitable cationic amphiphilic compounds are described by Kabanov A. V. et al in Bioconjugate Chem. (1995), 6(1), 7–20, the content of which is incorporated herein by reference.

According to a further aspect of the invention there is provided an oral vaccine comprising a nucleic acid encoding an antigen complexed to and/or entrapped within liposomes formed from liposome forming components including at least one cationic compound and at least one zwitterionic phospholipid characterised in that the liposome forming components include at least 25 mole %, preferably at least 50 mole %, of components which individually have a transition temperature of more than 40° C.

In this aspect of the invention the effect of using relatively high levels of high transition temperature lipidic components is that the transition temperature of the mixture of liposome for using components will be above 37° C. The transition temperature of a mixture tends to be close to the averaged transition temperatures of the individual components. However it is generally easier to determine the transition temperature of individual components, the values for many of these being known. Preferred high transition temperature zwitterionic phospholipids are DPPC ($T_c$ 41.4° C.), DSPC ($T_c$ 55.1° C.), DPPE ($T_c$ 64° C.) and DSPE ($T_c$ 74.2° C.).

In all aspects of the invention other components may be included in the liposome forming mixture, such as cholesterol, in amounts up to 50% by weight. Preferably the liposome forming components are free of cholesterol.

The amount of cationic compound is preferably in the range 5 to 50% of the total moles of liposome forming components, preferably in the range 10 to 25% mole.

The liposome composition is generally in the form of an aqueous suspension for instance, a physiological buffer. Alternatively it could be a dried composition for rehydration.

The liposomes may be made by any of the generally used liposome forming techniques. The product liposomes may be multilamellar or unilamellar vesicles and may be relatively large (vesicle diameters in the range 300 nm to 2000 nm preferably with average diameters in the range 500–1000 nm), or small (vesicle diameters in the range 100 nm to 400 nm preferably with average diameters in the range 200 to 300 nm). Preferably the liposomes have a mean diameter not exceeding 1000 nm, and preferably substantially all have diameters less than 2000 nm. Most preferably the mean diameter is in the range 200–750 nm.

In the novel compositions the nucleic acid may be complexed with liposomes that is located externally of the liposomes. Preferably, however, the nucleic acid is at least partially entrapped.

Preferably the liposomes are formed by a process in which the vesicles are formed, mixed with nucleic acid to be entrapped and are then dehydrated, preferably by freeze drying, and subsequently rehydrated in aqueous composition to make dehydration-rehydration vesicles (DRV's), optionally the DRV's may be subsequently subjected to microfluidization to reduce the average size. However, preferably the DRV's are not subjected to microfluidisation, or to only one or two cycles of microfluidisation. Preferably the nonentrapped material is separated from liposomes by centrifugation or molecular sieve chromatography, after the rehydration and/or microfluidization steps, although this may be unnecessary.

According to a further aspect of the present invention there is provided a method of entrapping polynucleotide into liposomes involving the steps of:
  i) forming an aqueous suspension comprising naked polynucleotide, which operatively encodes an immunogenic polypeptide useful to induce a desired immune response in a human or animal subject, and preformed liposomes formed of liposome forming components as specified for the novel compositions above,
  ii) freeze drying or spray drying the suspension, and
  iii) rehydrating the product of step ii) to form dehydration/rehydration vesicles.

Further steps which may be carried out but are not essential are:

iv) subjecting the aqueous suspension of dehydration rehydration vesicles from step iii to microfluidization to control the size; and/or v) optionally separating non entrapped polynucleotide from liposomes.

Step iv) is generally found to be unnecessary since the dehydration rehydration vesicles.

The last step is generally found to be unnecessary, since the external nucleic acid may be partially protected from the environment by being complexed to the cationically charged liposomes.

The dehydration-rehydration of steps are substantially as described by Kirby and Gregoriadis, (1984) Biotechnology, 2, 979–984, the content of which is incorporated herein by reference. Thus, the liposomes in step i) are preferably small unilamellar (SUV's) (although they may be MLV's for instance having size 2 µm) and made in step iii) are preferably multilamellar liposomes (MLV's) respectively. The product liposomes of step iii) are generally called dehydration-rehydration vesicles (DRV's).

Microfluidization of the DRV's is carried out substantially as described in WO-A-92/04009, the disclosure of which is incorporated herein by reference and by Gregoriadis et al, (1990), Int. J. Pharm. 65, 235–242. As mentioned above, if microfluidisation is conducted, it is preferred that no more than one of two cycles are conducted.

The present invention does not involve polymerising the liposome forming components to raise the transition temperature. This may reduce the delivery rate of active and is an undesirable extra step in the processing.

By using the DRV technique, inventors have established that up to 90% or even more of the polynucleotide present in the aqueous suspension subjected to the drying step can be entrapped into and/or complexed with the liposomes. The level of polynucleotide entrapment and/or complexing in the liposomal composition is preferably in the range 0.05 to 100, preferably 1 to 50, more preferably 5 to 50 µg/µ mole lipid.

The liposome compositions of the invention have been found to be resistant to bile salts and this is believed to correlate with stability in the GI tract.

The nucleic acid active may be RNA, for instance which is directly transcribable and translatable in the synthesis of the antigen, or which must first be reverse transcribed to form DNA for replication. Preferably the nucleic acid is DNA which is preferably replicated, and is transcribed and translated to form the antigen of choice. The DNA is preferably a ds plasmid DNA.

The invention includes also the use of the compositions of liposomes or made by the processes of the invention in the manufacture of a composition for use in a method of therapy or prophylaxis. For instance the method may be the immunisation (vaccination) of a human or animal subject to protect it against infection by infectious micro organisms. Alternatively an immune response may be generated by the gene product which is useful in immune therapy, for instance to treat cancer or other diseases, including infections.

EXAMPLES

The invention is illustrated further in the following examples:

Example 1

Methodology: Oral Immunisation Experiment 1
Liposome Preparation
Liposomes with the following compositions were prepared using the Dehydration-Rehydration method (DRV);

1) 32 µmoles of egg phosphatidylcholine (PC), (mixture of di fatty acyl phosphatidylcholines, including some saturated groups)
   16 µmoles of dioleoyl phosphatidylethanolamine (DOPE),
   8 µmoles of dioleoyl trimethylammonium propane (DOTAP).
2) 32 µmoles of distearoyl phosphatidylcholine (DSPC),
   16 µmoles of DOPE,
   8 µmoles of DOTAP.
3) 32 µmoles of DSPC,
   16 µmoles of cholesterol (CHOL),
   8 µmoles of DOTAP.
600 µg of pRc/CMV HBS plasmid DNA encoding for the S (small) region of Hepatitis B surface antigen (HBsAg; subtype ayw) was entrapped in the above liposome formulations using the following technique.

The dehydration-rehydration procedure (Kirby and Gregoriadis, (1984) op. cit.) was used for the incorporation of pRc/CMV HBS plasmid DNA into liposomes. In short, 2 ml of small unilamellar vesicles (SUV) were prepared from the specified liposome forming components mixed with plasmid DNA frozen at −20 C and freeze-dried overnight. The liposomes were then subjected to controlled rehydration to generate multilamellar (Gregoriadis et al, (1993) Biochim. Biophys. Acta 1147, 185–193) dehydration-rehydration vesicles (DRV). The product was not subjected to steps to remove non-entrapped DNA and probably includes external DNA complexed to the liposomes. No microfluidisation was conducted.

Entrapment complexation efficiency for each of the compositions was 85–95%, as determined by using $^{35}$S-labelled DNA, produced from $^{35}$S-dATP. The DRV's had mean diameters in the range 550 to 750 nm.

Immunisation

The method is based on Roy, K. et al (1999) Nature Medicine 5(4) 387–391.

Groups of 4 female Balb/c mice (20–24 g) were immunised orally with either "naked" (group 4) or liposome-entrapped (groups 1–3) DNA using animal feeding needles attached to a 1 ml syringe. Each mouse was fed with 100 µg of DNA in a volume of 500 µl of phosphate buffered saline (PBS) on days 0, 28 and 38.

Immunisation Groups:
1) PC:DOPE:DOTAP (100 µg DNA) (invention)
2) DSPC:DOPE:DOTAP (100 µg DNA) (invention)
3) DSPC:CHOL:DOTAP (100 µg DNA) (invention)
4) "Naked" DNA (100 µg DNA) (reference)
5) Control (no DNA)

IgA Extraction from Foecal Pellet

Foecal pellets were collected from the cages of mice on days 0, 14, 21, 32, 40, 48, 62, 84, 96 and 119.

These pellets were suspended in PBS at a concentration of 100 mg/ml, subjected to centrifugation and the supernatant (containing IgA) was analysed.

ELISA Measurements

ELISA was done on foecal extracts to measure secretory IgA. Plates were coated with the S (small) region of Hepatitis B surface antigen (HBsAg; subtype ayw), blocked with 1% BSA to avoid nonspecific binding and then pellet extracts added in duplicate (undiluted). Horseradish peroxidase-conjugated goat anti-mouse IgA was added, followed by o-phenylenediamine substrate. Absorbance at 450 nm was measured. Results in FIGS. 1a–i represent mean of duplicate measurements for each group of mice.

Example 2

Methodology: Oral Immunisation Experiment 2

Liposome Preparation

Liposomes with the following compositions were prepared using the Dehydration-Rehydration method (DRV):
1) 32 µmoles of DSPC,
   16 µmoles of DOPE,
   8 µmoles of DOTAP.
2) 32 µmoles of DSPC,
   16 µmoles of distearoyl phosphatidylethanolamine (DSPE),
   8 µmoles of DOTAP.
3) 32 µmoles of DSPC,
   16 µmoles of dipalmitoyl phosphatidylcholine (DPPE),
   8 µmoles of DOTAP.
4) 32 µmoles of DSPC,
   16 µmoles of DOPE.

pRc/CMV HBS plasmid DNA was entrapped into the above liposome formulations using the same method as Example 1. DRV compositions 1, 2 and 3 entrapped 85–95% of the total amount of DNA used. The noncationic DRV liposomes (composition 4) had an entrapment efficiency of 45–55% (of the total amount of DNA used). The DRV liposome sizes were in the same range as in Example 1.

Immunisation

Groups of 4 female Balb/c mice (20–24 g) were immunised orally with either "naked" (group 6) or liposome-entrapped (groups 1–5) DNA using animal feeding needles attached to a 1 ml syringe. Each mouse was fed with either 50 µg (group 5) or 100 µg (groups 1, 2, 3, 4 and 6) of DNA in a volume of 500 µl of PBS on days 0, 32.

Immunisation Groups:
1) DSPC:DOPE:DOTAP (100 µg DNA) (invention)
2) DSPC:DSPE:DOTAP (100 µg DNA) (invention)
3) DSPC:DPPE:DOTAP (100 µg DNA) (invention)
4) DSPC:DOPE (100 µg DNA) (reference)
5) DSPC:DOPE:DOTAP (50 µg DNA) (invention)
6) "Naked"DNA (100 µg DNA)
7) Control (no DNA)

IgA Extraction from Foecal Pellet

Foecal pellets were collected from the cages of mice on days 0, 42, 55, 65 and 92. These pellets were suspended in PBS at a concentration of 100 mg/ml, subjected to centrifugation and the supernatant (containing IgA) was analysed.

ELISA Measurements

ELISA was performed on fecal extracts to measure secretory IgA as for the first oral immunisation experiment. As for the first experiment, results in FIG. 2 a–d represent the mean of duplicate measurements for each group of mice.

Oral Immunisation Experiment 3

This experiment aims to investigate further the influence of the liposome composition on liposome-mediated oral immunisation. Two factors were measured:
1) The influence of the combination of the presence of phosphatidylcholine and cholesterol in the bilayer.
2) The effect of substituting the cationic dioleoyl trimethylammonium propane with cholesterol 3β-N-(dimethyl-aminoethyl)carbamate (DC-Chol)

Methodology:

Liposome Preparation

Liposomes with the following compositions were prepared using the Dehydration-Rehydration method (DRV), as described above in Example 1.
1) 32 µmoles of phosphatidylcholine (PC),
   16 µmoles of dioleoyl phosphatidylethanolamine (DOPE),
   8 µmoles of dioleoyl trimethylammonium propane (DOTAP).
2) 32 µmoles of distearoyl phosphatidycholine (DSPC),
   16 µmoles of DOPE,
   8 µmoles of DOTAP.
3) 32 µmoles of PC,
   16 µmoles of cholesterol (CHOL),
   8 µmoles of DOTAP.
4) 32 µmoles of DSPC
   16 µmoles of cholesterol (CHOL)
   8 µmoles of Cholesterol 3β-N-(dimethyl-aminoethyl) carbamate (DC-CHOL).

600 µg of pRc/CMV HBS plasmid DNA encoding for the S (small) region of Hepatitis B surface antigen (HBsAg; subtype ayw) was entrapped in the above liposome formulations. Entrapment efficiency for each of the compositions was 85–95%. The DRV diameters were in the same range as in Example 1.

Immunisation

Groups of 4 female Blab/c mice (20–24 g) were immunised orally with either "naked" (group 4) or liposome-entrapped (groups 1–4) DNA using animal feeding needles attached to a 1 ml syringe. Each mouse was fed with 100 µg of DNA in a volume of 500 µl of PBS on days 0, 28 and 38.

Immunisation Groups:
1) PC:DOPE:DOTAP (100 µg DNA)
2) DSPC:DOPE:DOTAP (100 µg DNA)
3) PC:CHOL:DOTAP (100 µg DNA)
4) DSPC:DOPE:DC-Chol (100 µg DNA)
5) "Naked" DNA (100 µg DNA)

IgA Extraction from Fecal Pellet

Fecal pellets were collected from the cages of mice on days 0, 30, 45, 60, 70.

These pellets were in PBS at a concentration of 100 mg/ml, subjected to centrifugation and the supernatant (containing IgA) was analysed.

ELISA Measurements

ELISA was done on fecal extracts to measure secretory IgA. Plates were coated with the S (small) region of Hepatitis B surface antigen (HBsAg; subtype ayw), blocked with 1% BSA to avoid nonspecific binding and then pellet extracts added in duplicate (undiluted). Horseradish peroxidase-conjugated goat anti-mouse IgA was added, followed by o-phenylenediamine substrate. Absorbance at 450 nm was measured. Results represent mean of duplicate measurements for each group of mice.

Results

Excreted IgA immune responses measured 60 and 70 days after the first dose are shown in FIGS. 1 and 2 respectively. Results show DRV composed DPSC:DOPE:DOTAP enhanced the highest responses in orally immunised mice at both time points. Replacement of the cationic lipid DOTAP with DC-CHOL in the liposome entrapped DNA results in lower anti-HBsAg IgA immune responses. Further, liposomes composed of PC:CHOL:DOTAP were also less effective than those composed of DSPC:DOPE:DOTAP in mediating immune responses.

Conclusions

The conclusions to be drawn from Examples 1 to 3 are that the experiments are repeatable. Furthermore it appears that relatively low levels of entrapped DNA provide adequate transfection rates for an immune response (comparing groups 1 and 5 of Example 2). The saturated lipids seem to produce liposomes having better performance.

Example 4

Reporter Gene Expression after Oral Dosing

Aim

To compare levels of gene expression in mesenteric lymph node after oral dosing of mice with either naked or liposome-entrapped plasmid DNA encoding fluorescent green protein reporter gene (pCMV.efgp). If the reporter gene is expressed, as indicated by visible green protein in recovered lymph nodes, this is an indication that the DNA reaches the mesenteric lymph nodes and is there endocytosed and expressed. Antigen presenting cells are located in the lymph nodes, the target for gene vaccines to generate an immune response.

Methodology:

Liposome Preparation

Liposomes composed of 32 μmoles of DSPC, 16 μmoles of DOPE, 8 μmoles of DOTAP were prepared using the Dehydration-Rehydration method (DRV) as described for example 1 and 600 μg of pCMV.efgp plasmid DNA entrapped.

Dosing and Measurement of Gene Expression

2 female Balb/c mice (20–24 g) were dosed orally with either "naked" or liposome-entrapped DNA using animal feeding needles attached to a 1 ml syringe. Each mouse was fed with 100 μg of DNA in a volume of 500 μl of PBS. 44 h after dosing, mesenteric lymph nodes were collected from dosed and control (naive) mice. The freshly collected lymph nodes were adhered to Cryostat chucks using Tissue-Teck (Miles Inc, USA), then frozen in liquid nitrogen. Sections were cut at 20 μm in a Slee Cryostat. Images were captured under Nikon microphoto Microscope, using incident fluorescence and Kodak ektachrome 4000 ASA.

RESULTS AND CONCLUSIONS

Figure 1A:
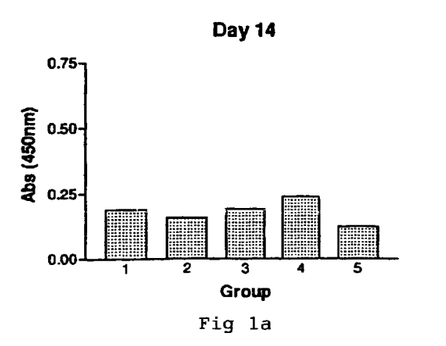
FIGS. 1a through 1i are graphs of absorbance from day 14 through day 119.
Figure 1B:
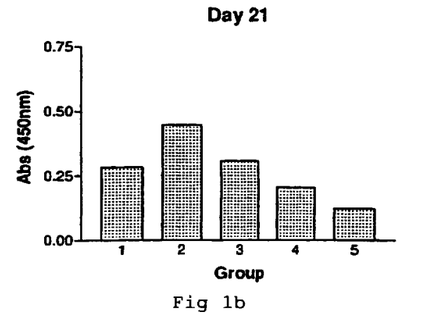
Figure 1C:
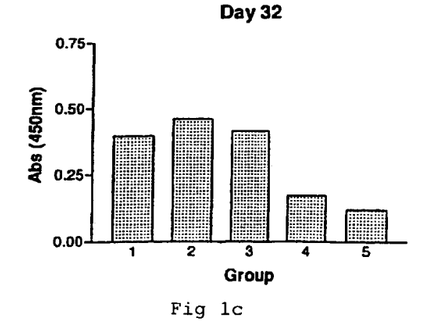
Figure 1D:
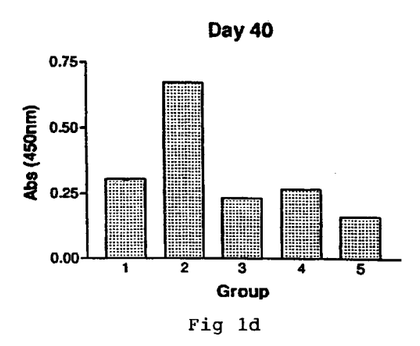
Figure 1E:
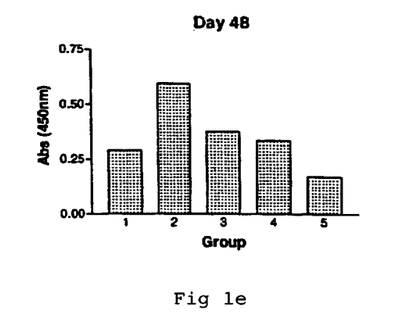
Figure 1F:
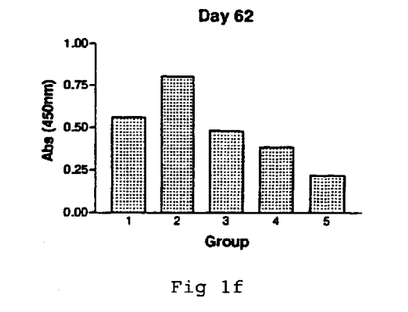
Figure 1G:
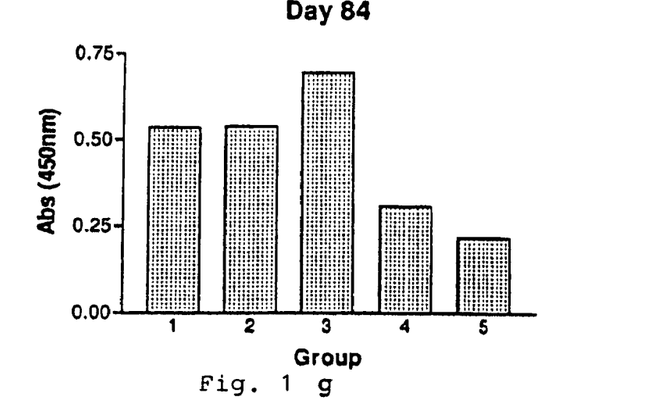
Figure 1H:
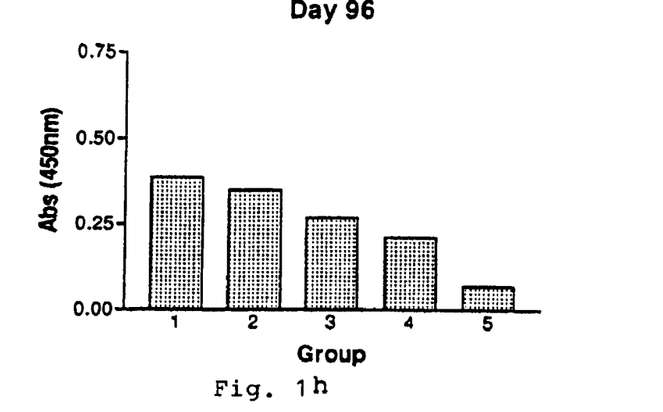
Figure 1I:
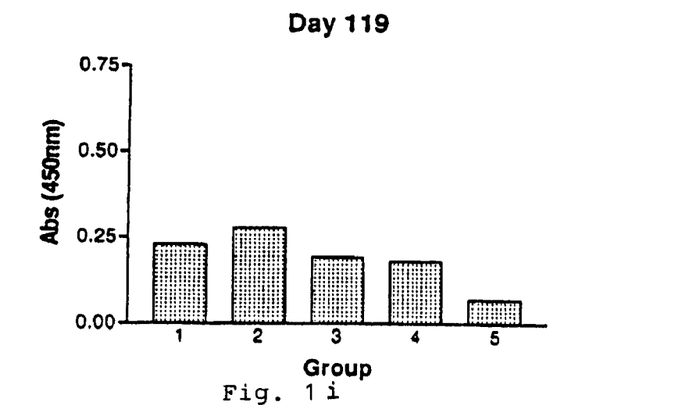
Figure 2A:
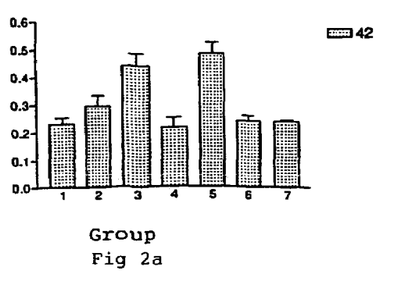
FIGS. 2a through 2d show the mean of duplicate measurements for groups of mice.
Figure 2B:
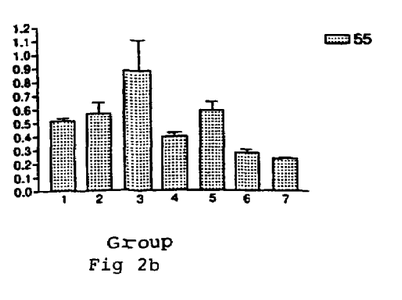
Figure 2C:
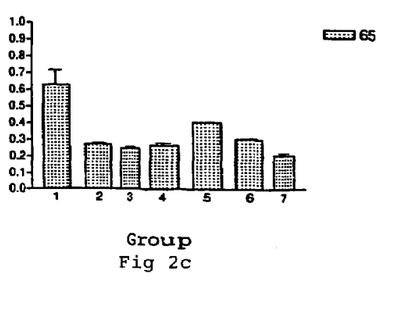
Figure 2D:
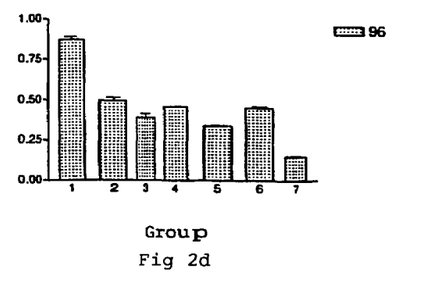
Figure 3A:
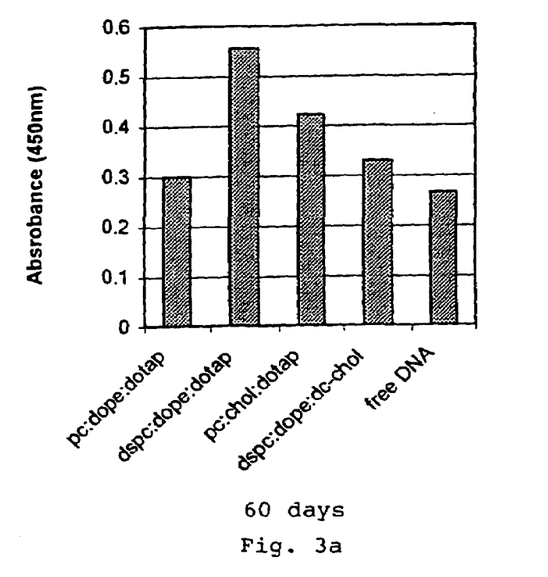
FIGS. 3a and 3b are graphs of absorbance at 60 and 70 days, respectively.
Figure 3B:
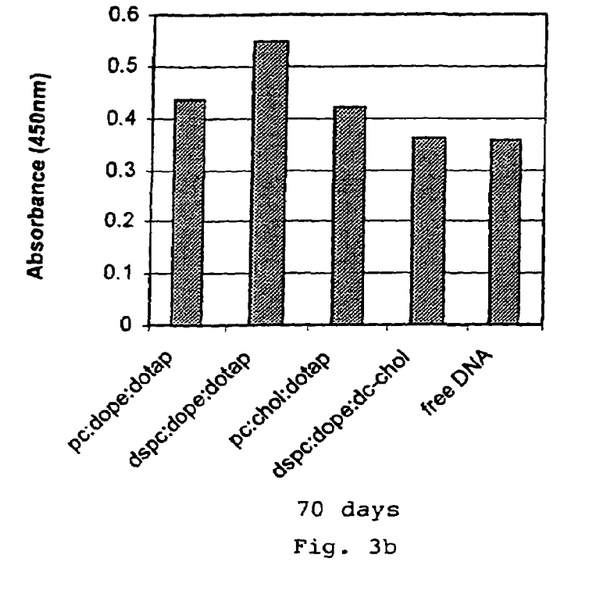
Figure 4A:
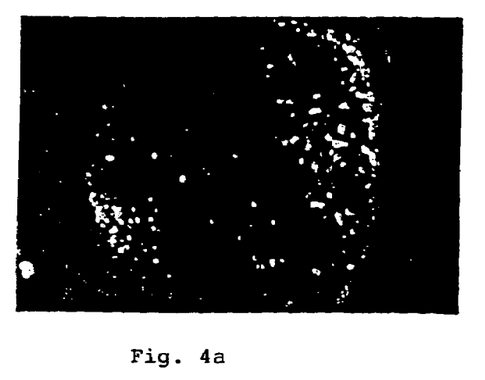
FIGS. 4a, 4b and 4c show mice lymph nodes dosed with the invention, naked DNA and background.
Figure 4B:
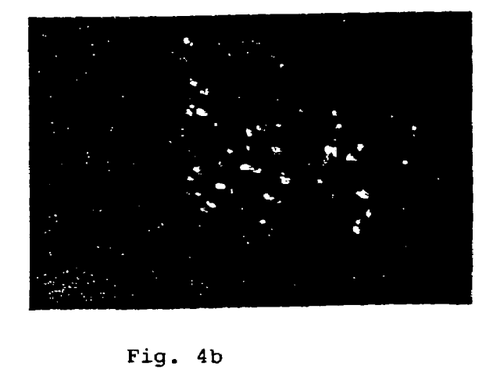
Figure 4C:
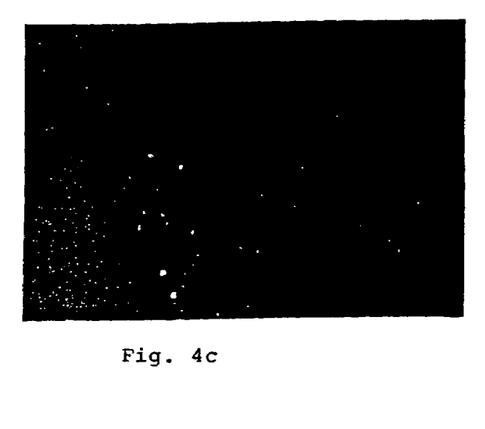

Higher levels of the plasmid encoded fluorescent green protein can be seen in the mesenteric lymph nodes of mice dosed with liposome-entrapped pCMV.efgp (FIG. 4a) compared to those which received naked pCMV.efgp (FIG. 3b) and background levels as shown in lymph node sections taken from naive mice (FIG. 3c). From this it may be concluded that orally administered DNA is cleared to the mesenteric lymph node and that the rate of expression of reporter gene in the mesenteric lymph node is increased by encapsulation in cationic liposomes comprising saturated lipids. This is consistent with the results showing the increase in immune response by entrapment in cationic liposomes formed from saturated lipids.

The invention claimed is:

1. Method of eliciting an IgA response in a mammal comprising administering orally to the mammal a composition comprising a nucleic acid operatively encoding an antigen complexed with or entrapped within liposomes formed from liposome forming components comprising
   a) at least one cationic compound
   b) zwitterionic phospholipid consisting of one or two compounds having the general formula II in which $R^3$ and $R^4$ are the same or different and are a group of the formula $CH_3(CH_2)_e(CH=CH-H_2)_f(CH_2)_g$ — in which f is 0 to 6, each of e and g+3f are 0 to 23 and e+g is in the range 12 to 23;

$R^7$ is a $C_{1-8}$ alkanediyl group;

Y is —O— or a bond;

$X^2$ is N, P or S;

m is 3 when $X^2$ is N or P and is 2 when $X^2$ is S; and the groups $R^8$ are the same or different and are selected from the group consisting of hydrogen, $C_{1-8}$ alkyl, $C_{6-11}$ aryl or aralkyl, or two or three of the groups $R^8$ together with $X^2$ form a saturated or unsaturated heterocyclic group having 5 to 7 ring atoms;

in which at least 25% by mole of the individual liposome forming components have a transition temperature of more than 40° C., wherein the molar ratio of cationic compound to zwitterionic phospholipid is in the range 1:1 to 1:10, whereby an IgA response to the said antigen is generated.

2. A method according to claim 1 in which the cationic compound has the general formula I, $$R^1OCH_2CH(OR^2)CH_2R^5X^1R^6_n \qquad I$$

in which $R^1$ and $R^2$ are the same or different and are a group of the formula $CH_3(CH_2)_a(CH=CH-CH_2)_b(CH_2)_c(CO)_d$ — in which b is 0 to 6, a and c are each selected from 0–23 and (a+c+3b) is in the range 12–23 and d is 0 or 1;

$R^5$ is a bond or a $C_{1-8}$ alkanediyl group;

$X^1$ is N, P or S;

n is 3 where $X^1$ is N or P and is 2 where $X^1$ is S; and the groups $R^6$ are the same or different and are selected from the group consisting of hydrogen, $C_{1-8}$ alky, $C_{6-12}$ aryl and aralkyl, or two or three of the groups $R^6$ together with $X^1$ form a saturated or unsaturated heterocyclic group having 5 to 7 ring atoms.

3. A method according to claim 2 in which $R^1$ is the same as $R^2$ and $R^3$ is the same as $R^4$.

4. A method according to claim 3 in which $R^1$ and $R^2$ represent a different group to $R^3$ and $R^4$.

5. A method according to claim 3 in which $R^1$ and $R^2$ represent a different group to $R^3$ and $R^4$, in which in $R^1$ and $R^2$, b is 1, and in which (a+c) is in the range 10 to 20.

6. A method according to claim 1 in which the liposome forming materials comprise two zwitterionic phospholipids in each of which Y is O, $X^2$ is N, and the groups $R^8$ of the first phospholipid are all hydrogen and the groups $R^8$ of the second phospholipid are all $C_{1-14}$ alkyl, and $R^7$ is $(CH_2)_h$ in which h is 2 or 3.

7. A method according to claim 6 in which the groups $R^3$ and $R^4$ of the said first phospholipid are the same and each is a group in which f is 1 and (e+g) is in the range 10 to 20.

8. A method according to claim 7 in which in the groups $R^3$ and $R^4$ of the said second phospholipid are the same and each is a group in which f is 0 and e+g is in the range 15 to 23.

9. A method according to claim 8 in which the said second zwitterionic phospholipid is selected from the group consisting of distearoylphosphatidylcholine, distearoylphosphatidylethanolamine, dipalmitoylphosphatidylcholine and dipalmitoylphosphatidylethanolamine.

10. A method according to claim 1 in which the cationic compound is cholesterol-3β-N-(dimethylaminoethyl)carbamate.

11. A method according to claim 1 in which the nucleic acid is entrapped within the liposomes.

12. A method according to claim 1 in which the mammal is a human.

13. A method according to claim 1 in which in the groups $R^3$ and $R^4$ of at least one phospholipid are the same.

14. A method according to claim 13 in which the mammal is a human.

15. A method according to claim 14 in which at least 50% by mole of the individual liposome forming components have a transition temperature of more than 40° C.

16. A method according to claim 13 in which there are two phospholipid compounds and the groups $R^3$ and $R^4$ in each phospholipid are the same.

17. A method according to claim 1 in which at least 50% by mole of the individual liposome forming components have a transition temperature of more than 40° C.

18. A method according to claim 2 in which in the groups $R^3$ and $R^4$ of at least one phospholipid are the same.

19. A method according to claim 18 in which the mammal is a human.

20. A method according to claim 18 in which there are two phospholipid compounds and the groups $R^3$ and $R^4$ in each phospholipid are the same.

* * * * *